United States Patent [19]

Hall

[11] Patent Number: 5,234,003
[45] Date of Patent: Aug. 10, 1993

[54] FLEXIBLE TIP WIRE GUIDE

[75] Inventor: Todd A. Hall, Bloomington, Ind.

[73] Assignee: Cook Incorporated, Bloomington, Ind.

[21] Appl. No.: 839,340

[22] Filed: Feb. 20, 1992

[51] Int. Cl.⁵ ................................ A61B 5/00
[52] U.S. Cl. ........................... 128/772; 128/657
[58] Field of Search ............... 128/657, 772; 604/95, 604/164, 280-283

[56] References Cited

U.S. PATENT DOCUMENTS

| | | | |
|---|---|---|---|
| 3,789,841 | 2/1974 | Antoshlaw | 128/772 |
| 4,721,117 | 1/1988 | Mar et al. | 128/772 |
| 4,748,986 | 6/1988 | Morrison et al. | 128/657 |
| 4,763,647 | 8/1988 | Gambale | 128/657 |
| 4,832,047 | 5/1989 | Sepetka et al. | 128/657 |
| 4,922,924 | 5/1990 | Gambale et al. | 128/657 |

Primary Examiner—Max Hindenburg
Attorney, Agent, or Firm—Richard J. Godlewski

[57] ABSTRACT

A wire guide having a generally increasing flexible tip that is resistant to fracture. The flexible tip wire guide comprises a cylindrical wire member having a substantially uniform outer diameter main portion and a distal portion with a tapered outer surface region for gradually increasing the flexibility of the tip and a proximal concave outer surface region that extends tangentially and proximally from the tapered outer surface for increasing the fracture resistance of the decreasing outer diameter distal portion. A flexible wire coil is inserted over the distal wire portion and secured to the proximal end of the distal wire portion and the distal end of the main portion using silver solder with a uniform outer diameter for minimizing potential trauma to vessel walls. The outer diameter of the flexible wire coil is substantially equivalent to the outer diameter of the main portion of the wire guide to likewise minimize trauma to vessel walls. A cylindrical outer surface extends distally from the tapered outer surface of the distal wire portion to add uniform flexibility to the flexible tip for use, e.g., in a J-tip configuration. The distal end of the flexible wire coil is attached to the distal end of the distal wire portion with silver solder or a weld that is hemispherically shaped for minimizing trauma during insertion through the vessel.

20 Claims, 1 Drawing Sheet

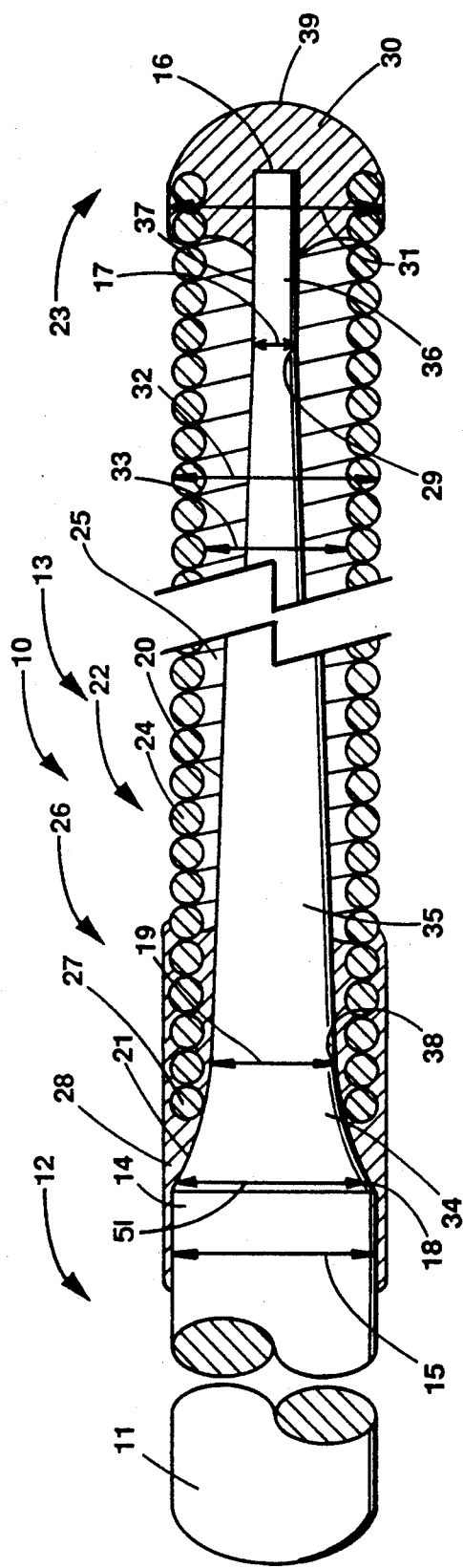
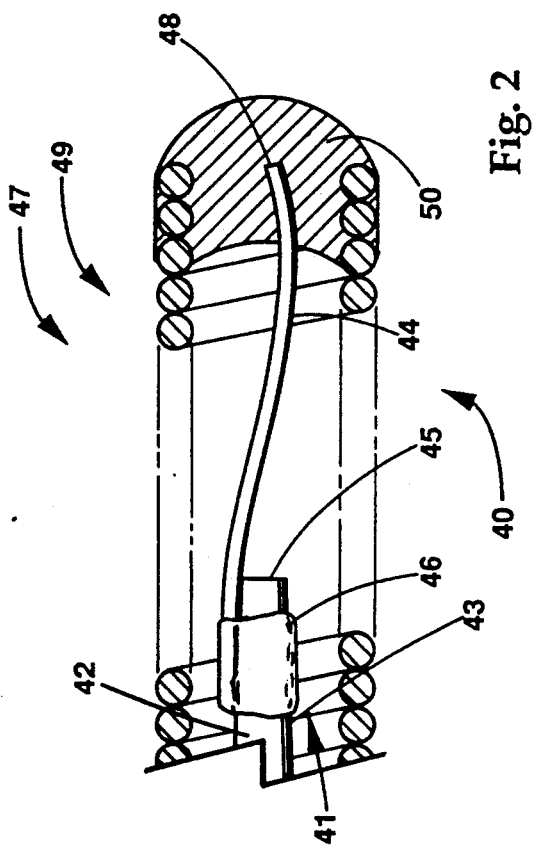

FLEXIBLE TIP WIRE GUIDE

TECHNICAL FIELD

This invention relates generally to medical devices and, in particular, to a flexible tip wire guide having gradually increasing flexibility along the distal portion thereof that is resistant to fracture.

BACKGROUND OF THE INVENTION

The use of a small diameter wire guide in the vessel of a patient such as the coronary vessels facilitates placement of a guiding catheter or another medical device thereover to the treatment site.

One flexible wire guide for use in cardiovascular procedures includes an elongated shaft with a coil spring mounted on the distal end of the shaft. The elongated shaft has a tapered portion near the distal end to gradually increase the flexibility of the distal end of the wire guide. The elongated shaft also includes a stepped down or significantly reduced diameter portion that is positioned proximal the tapered portion. The stepped down portion is typically formed by plunge grinding, which causes abrupt shoulders at the junctions with the main and tapered portions of the shaft. The coil spring is attached to the elongated shaft around the stepped down portion. The stepped down portion provides a recess for positioning the coil spring therearound and flowing solder therein to fixedly position the coil. In addition, the outer diameter of the wire guide about the proximal end of the coil spring remains constant for preventing a catheter from catching on the wire guide as the catheter is advanced thereover. A problem with this flexible wire guide is that the abrupt shoulder at the end of the stepped down portion of the shaft provides a stress point at which a fracture is prone to occur through the reduced diameter. This problem is compounded by the soldering of the coil spring to the stepped down portion, which heats or anneals the stepped down portion and further weakens the stepped down portion of the shaft. In use, the proximal end of the wire guide is rotated and advanced through the vessels of the vascular system, while the distal end bends and flexes. When stress is applied to the weakened portion of the elongated shaft, the shaft can fracture and break. As a result, the distal portion of the wire guide including the coil spring is deposited in the vascular system of the patient. This fragmented portion of the wire guide must be removed using a retrieval device or more invasive methods such as open surgery.

Another steerable wire guide includes a main core wire that is ground down near its distal end to form a shoulder and a reduced diameter, cylindrical distal region of increased, uniform flexibility. The wire guide also includes a coil that is welded to the shoulder region for facilitating a relatively smooth transition between the outer surface of the main core wire and the proximal end of the coil. A problem with the use of this wire guide is that the distal region has an abrupt change in flexibility rather than a continued increase in flexibility toward the distal end. If the distal region is too flexible, it deflects and will not track the vessel wall. If the distal region is too stiff, the risk of vessel perforation is significant. In addition, the distal end of the wire guide having an abrupt change in flexibility is easily dislodged from the target vessel and moves around as the catheter is advanced over the guide. Thus, the difficulty in inserting a catheter over the wire guide into a branching or target vessel is compounded and often thwarted with the dislodged guide. Another problem with the use of this wire guide is that the ground down shoulder has an abrupt, sharp radius. Again, the abrupt reduction in diameter weakens the main core wire at the point of attachment of the coil. The weakened point in the core wire is subjected to stress caused by the bending coil and, as a result, the wire guide can break at that point, depositing the distal region of the wire guide in the vessel of a patient, as previously described.

SUMMARY OF THE INVENTION

The foregoing problems are solved and a technical advance is achieved in an illustrative wire guide having a tip which gradually increases in flexibility. The distal portion of the wire guide is advantageously formed with a gradually decreasing diameter that gradually increases flexibility and significantly resists fracturing. The guide comprises an elongated cylindrical wire member having a main portion and a distal portion. The distal portion includes distal and proximal ends with a first, substantially uniform outer diameter about the distal end, a second larger, substantially uniform outer diameter near the proximal end, and a third, substantially uniform outer diameter at the proximal end. The third outer diameter at the proximal end of the distal portion is substantially equivalent to the outer diameter at the distal end of the main portion. The distal portion decreases in diameter between the first and second outer diameters with, for example, a conically tapered outer surface region therebetween. The distal portion also includes a concave outer surface that extends between the second and third outer diameters at and near the proximal end of the distal portion. In another aspect, the concave outer surface region extends distally from the distal end of the main portion to the tapered region with a blend therebetween. These tapered and concave outer surface regions are tangential to form the blend which advantageously reduces stress thereat and the possibility of fracture. A flexible coil having a maximum outer diameter substantially equivalent to the outer diameter of the distal portion is positioned over the main portion of the wire member and attached thereto with fastening means such as silver solder.

The inner diameter of the flexible coil is advantageously greater than the outer diameter along the tapered outer surface region of the distal wire portion to permit the proximal turn of the coil to be positioned adjacent the concave outer surface of the distal wire portion. This further advantageously reduces the stress applied to the blend and further reduces the possibility of wire fracture. The fastening means comprising, for example, silver solder extends longitudinally and distally from the proximal end of the distal wire portion a predetermined distance to secure the proximal end of the flexible coil to the distal portion of the wire member. This fastening means can also extend proximally from the distal end of the main portion for providing strength to the union of the coil with the wire member. The fastening means has a maximum outer diameter along the length of the union for advantageously minimizing trauma to vessels when inserted therethrough.

The distal turns of the flexible wire coil are stretched to relax these turns and provide further flexibility to the distal tip portion. The distal ends of the distal wire portion and flexible wire coil are secured to one another with a second fastening means such as silver solder or a weld having a hemispherically surfaced tip for minimizing trauma to vessel walls.

The distal wire portion further includes a uniform cylindrical outer surface extending distally from the tapered outer surface region to the distal end of the distal wire portion. This advantageously provides a uniform flexibility region to form the straight tip of a well-known J-tip configuration which enhances directability into branch vessels. An attached safety wire is substituted for this cylindrical outer surface region to add more, uniform flexibility to the distal turns of the coil extending to the tip of the wire coil. As a result, a floppy distal end tip is provided. To advantageously increase fracture resistance, the concave outer surface of the distal wire portion is uniformly radiused between the tapered outer surface and the main portion of the wire member.

BRIEF DESCRIPTION OF THE DRAWING

FIG. 1 depicts an illustrative flexible tip wire guide of the present invention; and FIG. 2 depicts another aspect of the flexible tip wire guide of the present invention.

DETAILED DESCRIPTION

FIG. 1 depicts a partially sectioned, illustrative flexible tip wire guide 10 for a traumatic and controlled advancement through the vascular system of a patient. In particular, this flexible tip wire guide has a fracture resistant tip portion and is ideally suited for advancement through small, tortuous blood vessels such as the coronary vessels for positioning another medical device such as a guiding catheter thereover. Wire guide 10 includes elongated cylindrical wire member 11 having a main, uniform diameter portion 12 that extends longitudinally nearly the entire length of the wire guide and a distal, decreasing diameter portion 13 that distally and gradually increases in flexibility. Flexible wire coil 22 is positioned about the distal portion and secured thereto about proximal end 18 using fastening means 28 such as silver solder. The coil has a maximum outer diameter 32 substantially equivalent to that of the wire member to maintain a relatively smooth, uniform outer diameter that does not catch on and traumatize the walls of the vessel. The fracture resistant distal portion of the wire member decreases in diameter through several different outer surface regions toward the distal end for providing a gradual increase in flexibility. Proximal region 34 has a uniformly radiused, concave outer surface 21; intermediate region 35 has a conically tapered outer surface 20; and distal region 36 has a cylindrical outer surface 37. The substantially uniform outer diameter coil is positioned over the distal portion and secured thereto for presenting an increasingly flexible, a traumatic surface to a vessel wall. The coil is preferably secured to the elongated cylindrical wire member about the distal and proximal ends of the respective main and distal portions for providing a substantially uniform outer diameter along the entire length of the wire guide without weakening the elongated cylindrical wire member at the union with the coil.

Main portion 12 of wire member 11 includes a substantially uniform outer diameter 15 at distal end 14. Cylindrical wire member 11 is, for example, 60 cm in length and comprises commercially available material such as nitinol or Series 302, 304, or 316 stainless steel. Other well-known lengths of wire guides include 100, 120, 180, 240, 360, 400, and 480 centimeters. Main portion 12 of wire member 11 is approximately 53 cm in length and 0.018" in diameter.

Distal portion 13 of the wire member is, for example, approximately 7 cm in length and extends between distal end 16 and proximal end 18, which abuts distal end 14 of main portion 12. Proximal 18 has a substantially uniform outer diameter 51 that is substantially equivalent to main portion outer diameter 15. Proximal region 34 of the distal portion extends between proximal end 18 and blend 38 and includes concave outer surface 21 with a uniform radius of approximately 0.025" extending longitudinally from proximal end 18 to proximal blend 38. Blend 38 has a substantially uniform outer diameter 19 of approximately 0.011" and begins at a longitudinal distance of approximately 0.013" from distal end 14 of the main portion and proximal end 18 of the distal portion. Intermediate region 35 of distal portion 13 extends between proximal blend 38 and distal blend 29, which is approximately 6 cm from proximal end 18, and includes conically tapered outer surface 20 that uniformly decreases in diameter from proximal blend 38 to distal blend 29. The distal blend has a substantially uniform outer diameter 17 of approximately 0.004" at the distal end of the intermediate region. Concave outer surface 21 extends tangentially and proximally from the tapered outer surface at blend 38 to enhance the fracture resistance of the guide. Concave outer surface 21 is also radiused at distal end 14 of the main portion and proximal end 18 of the distal portion to eliminate a sharp edge thereat. Distal region 36 of the distal portion extends longitudinally from distal blend 29 for approximately 1 cm and includes cylindrical outer surface 37 having an approximately 0.004" uniform outer diameter 17 of the distal portion that extends longitudinally about distal end 16 of the distal portion.

Flexible wire coil 22 includes proximal end 26, distal end 23, plurality of turns 24, and hollow passageway 25 extending longitudinally therein. Flexible wire coil 22 comprises, for example, commercially available 0.003" diameter metallic wire that is tightly wrapped and coupled to form turns 24 that are approximately the same length as distal portion 13. Wire turns 24 have very little, if any, spacing therebetween. The wire comprises, for example, platinum, a platinum alloy including 5 to 10 percent tungsten, or Series 302, 304, or 316 stainless steel. The flexible wire coil has maximum outer diameter 32 such as approximately 0.018" that is substantially equivalent to uniform outer diameter 15 of the main portion of elongated cylindrical wire member 11. The substantial equivalence of these outer diameters provides for a substantially uniform outer diameter of the wire guide and resists fracturing of the wire guide or catching the wire guide on a catheter being positioned thereover. The flexible wire coil has minimum inner diameter 33 such as approximately 0.012" that is at least equal to substantially uniform outer diameter 19 of the distal portion at proximal blend 38 for positioning distal portion 13 of the wire member in passageway 25 of the coil. The distal 2 to 4 cm of the coil turns are stretched approximately 2 to 8 cm depending on the tension of the coil in a well-known manner to relax the distal turns of the coil. The relaxed distal coil turns provide increased flexibility toward the distal end of the coil. The relaxed distal coil turns also present a more pliable, atraumatic surface than the tightly wrapped and coupled proximal coil turns.

Plurality of turns 24 of the flexible coil includes proximal turn 27 positioned at proximal end 26 of the coil.

The proximal end turn is positioned about proximal blend 38 of the distal portion and preferably tangent to concave outer surface 21 with the far most proximal end of the coil approximately 0.008" from proximal end 18 to reduce the stress at proximal blend 38.

Fastening means 28 such as silver solder extends longitudinally and distally a predetermined distance such as 2 to 4 mm from proximal end 18 of distal wire portion 13. The solder secures the very proximal turns of the coil to the proximal and intermediate regions of distal wire portion 13. Fastening means 28 also extends longitudinally and proximally a predetermined distance such as 1 to 4 mm from distal end 14 of main wire portion 12. Fastening means 28 has a maximum outer diameter of, for example, approximately 0.0185", which is within a predetermined tolerance of, for example, approximately 0.0005" of substantially uniform outer diameter 15 of main portion 12 or maximum outer diameter 32 of flexible coil 22. Although preferably depicted as coating the outer surface of the main portion about the distal end thereof, silver solder 28 need only extend from proximal end 18 of the distal wire portion to secure the wire coil thereto.

Distal end 16 of cylindrical distal wire portion 13 is secured to distal end 23 of the flexible coil by fastening means 30 such as silver solder or a well-known weld. Silver solder 30 forms a hemispherical tip 39 and is allowed to flow proximally up to 3 mm from distal end 23 of the coil. Outer diameter 31 of the solder is no larger than approximately 0.0185" so as to provide a uniform outer diameter along the length of the wire guide. Alternatively, fastening means 30 comprises a well-known weld, which typically includes melted stainless steel and platinum and is smaller in size than a silver solder tip.

Distal portion 13 of the wire guide has a slight curve formed therein, for example, by running the portion over an edge. This slight curvature allows the tip to be easily guided through a vessel by rotation of the wire guide. The distal portion can also be formed into a well-known J-tip configuration for directing the wire guide into branching vessels in a well-known manner by the attending physician. Cylindrical outer surface region 36 is ideally suited for the straight distal tip portion of the J-tip configuration.

Depicted in FIG. 2 is a partially sectioned view of the tip section of flexible tip wire guide 40, which represents another aspect of the present invention. Similar to the wire guide of FIG. 1, distal wire portion 41 of the elongated wire member is approximately 4 cm in length and includes a proximal region (not shown) and intermediate region 42 having a tapered outer surface 43. Safety wire 44 having an outer diameter of approximately 0.002" and being approximately 3 cm in length is secured about distal end 45 of distal wire portion 41, as shown, using silver solder 46. Flexible wire coil 47, as previously described, is approximately 7 cm in length and is positioned over the distal wire portion and attached to the proximal end thereof as previously described. Distal end 48 of the safety wire is secured to distal end 49 of the flexible wire coil using well-known fastening means 50 such as a hemispherically shaped weld. The safety wire adds further flexibility to the distal-most region of the wire guide and flexible wire coil.

It is to be understood that the above-described flexible tip wire guide is merely an illustrative embodiment of the principles of this invention and that other flexible tip wire guides may be devised by those skilled in the art without departing from the spirit and scope of this invention. It is contemplated that the elongated cylindrical wire member of the guide may be formed of other materials such as plastics which are of suitable strengths for insertion into the body. It is further contemplated that the flexible wire coil can be similarly fashioned of a polymer plastic material and secured to the elongated cylindrical wire member using a commercially available fastening means such as medical grade adhesive and the like. The distal tip of the guide may also be similarly fashioned or formed from these medical grade adhesives. It is further contemplated that a platinum wire coil can be inserted on a polymer wire member and affixed thereto using commercially available, medical grade adhesives. The concave outer surface of the proximal region of the distal wire portion may take on nonuniform shapes such as to provide a decreasing radius of the wire member toward the distal end. This concave outer surface is likewise blended so as to tangentially and longitudinally extend from the tapered outer surface and not present any stress line so as to facilitate fracture of the guide about the distal wire portion. The cylindrical outer surface of the distal wire portion can be eliminated such as to provide continuously increasing flexibility to the distal portion of the wire guide.

What is claimed is:

1. A flexible tip wire guide comprising:
an elongated member having a main portion and a distal portion, said main portion having a distal end with a substantially uniform outer diameter, said distal portion having a distal end with a first substantially uniform outer diameter, a proximal end, a second substantially uniform outer diameter near said proximal end greater than said first diameter, and a third substantially uniform outer diameter at said proximal end substantially equivalent to said outer diameter of said main portion, said distal portion also decreasing in diameter from said second to sad first outer diameter and including a concave outer surface about said proximal end extending between said second and third outer diameters;
a flexible coil having a distal end, a proximal end, a plurality of turns, a passageway extending longitudinally therein, a maximum outer diameter substantially equivalent to said outer diameter at said distal end of said main portion, and a minimum inner diameter at least equal to said second outer diameter of said distal portion, said distal portion of said elongated member positioned within said passageway of said coil, said proximal end of said coil including a proximal turn of said plurality of turns positioned about said second outer diameter of said distal portion of said elongated member; and
fastening means for securing said proximal end of said coil to said distal portion of said elongated member about said second outer diameter.

2. The guide of claim 1 wherein said proximal turn of said coil has an inner diameter greater than said second outer diameter of said distal portion and positioned adjacent said concave outer surface of said distal portion.

3. The guide of claim 1 wherein said fastening means extends longitudinally and distally from said proximal end of said distal portion a predetermined distance and secures said proximal end of said flexible coil to said distal portion of said elongated member.

4. The guide of claim 3 wherein said fastening means includes a maximum outer diameter along said distal portion of said elongated member and said flexible coil within a predetermined tolerance of said maximum outer diameter of said coil.

5. The guide of claim 1 wherein said fastening means extends longitudinally and proximally from said distal end of said main portion a first predetermined distance and longitudinally and distally from said first proximal end of said distal portion a second predetermined distance and secures said proximal end of said flexible coil to said elongated member.

6. The guide of claim 5 wherein said fastening means includes a maximum outer diameter within a predetermined tolerance of one of sad maximum outer diameter of said coil and said outer diameter of said main portion.

7. The guide of claim 1 wherein said plurality of turns of said flexible coil are relaxed about said distal end thereof.

8. The guide of claim 1 further comprising second fastening means for securing said distal end of said flexible coil about said distal end of said distal portion of said elongated member.

9. The guide of claim 8 wherein said second fastening means comprises silver solder.

10. The guide of claim 8 wherein said second fastening means comprises a weld.

11. The guide of claim 1 wherein said fastening means comprises silver solder.

12. A flexible tip wire guide comprising:
an elongated member having a main portion and a distal portion, said main portion having a distal end with a substantially uniform outer diameter, said distal portion having a tapered outer surface region, a concave outer surface region extending longitudinally and distally from said distal end of said main portion, and a blend positioned between said concave and tapered regions and having a substantially uniform outer diameter;
a flexible coil having a distal end, a proximal end, a plurality of turns, a passageway extending longitudinally therein, a maximum outer diameter substantially equivalent to said outer diameter of said main portion, and a minimum inner diameter at least equal to said outer diameter of said blend, said distal portion of said elongated member positioned within said passageway of said coil, said coil including a proximal turn of said plurality of turns positioned tangentially adjacent said concave outer surface region of said distal portion of said elongated member; and
fastening means for securing said proximal end of said coil to said distal portion of side elongated member about said outer diameter of said blend.

13. A flexible tip wire guide comprising:
an elongated cylindrical member having a main portion and a distal portion, said main portion having a distal end with a first substantially uniform outer diameter, said distal portion having a distal end with a first substantially uniform outer diameter, a proximal end, and a second substantially uniform outer diameter near said proximal end greater than said first diameter, said distal portion including a tapered outer surface extending longitudinally from said second to said first outer diameter and a concave outer surface extending tangentially and proximally from said tapered outer surface about said second outer diameter to said outer diameter at said distal end of said main portion;
a flexible coil having a distal end, a proximal end, a plurality of turns, a passageway extending longitudinally therein, a maximum outer diameter substantially equivalent to said outer diameter of said main portion, and a minimum inner diameter at least equal to said second outer diameter of said distal portion, said distal portion of said elongated member positioned within said passageway of said coil, said proximal end of said coil including a proximal turn of said plurality of turns positioned about said second outer diameter of said distal portion of said elongated member; and
fastening means for securing said proximal end of said coil to said distal portion of said elongated member about said second outer diameter.

14. The guide of claim 13 wherein said concave outer surface includes a uniform radius.

15. The guide of claim 13 wherein said proximal turn of said coil has an inner diameter greater than said second outer diameter of said distal portion and tangentially positioned adjacent said concave outer surface of said distal portion.

16. The guide of claim 13 wherein said distal portion includes a cylindrical outer surface extending distally from said tapered outer surface to said distal end of said distal portion.

17. The guide of claim 13 further comprising a safety wire fixedly attached about said distal end of said distal portion and extending distally therefrom.

18. The guide of claim 17 further comprising second fastening means for securing said distal end of said flexible coil to a distal end of said safety wire.

19. The guide of claim 13 wherein said fastening means extends longitudinally and distally from said proximal end of said distal portion a predetermined distance and secures said proximal end of said flexible coil to said distal portion of said elongated member.

20. A flexible tip wire guide comprising:
an elongated cylindrical wire member having a main portion and a distal portion, said main portion having a distal end with a substantially uniform outer diameter, said distal portion having a distal end, a first substantially uniform outer diameter about said second distal end, a proximal end, and a second substantially uniform outer diameter near said proximal end greater than said first diameter, said distal portion including a tapered outer surface and extending longitudinally from said second to said first outer diameter and a concave outer surface having a uniform radius extending tangentially and proximally from said tapered outer surface about said second outer diameter to said outer diameter at said distal end of said main portion, said distal portion also including a cylindrical outer surface extending distally from said tapered outer surface about said first outer diameter to said distal end of said distal portion;
a flexible wire coil having a distal end, a proximal end, a plurality of turns having relaxed distal turns about said distal end thereof and tightly coupled proximal turns about said proximal end thereof, a passageway extending longitudinally therein, a maximum outer diameter substantially equivalent to said outer diameter of said main portion, and a minimum inner diameter greater than said second outer diameter of said distal portion, said distal portion of said elongated member positioned within said passageway of said coil, said proximal end of said coil including a proximal turn of said plurality of turns positioned tangentially adjacent said concave outer surface of said distal portion of said elongated member;

first fastening means extending longitudinally and distally from said proximal end of said distal portion a first predetermined distance and longitudinally and proximally from said distal end of said main portion a second predetermined distance for securing said proximal end of said coil to said distal portion of said elongated member about said second outer diameter, said first fastening means including a maximum outer diameter within a predetermined tolerance of one of said maximum outer diameter of said coil and said outer diameter of said main portion; and second fastening means for securing said distal end of said coil to said distal end of said distal portion.

* * * * *